(12) United States Patent
Gerner et al.

(10) Patent No.: US 6,601,438 B2
(45) Date of Patent: Aug. 5, 2003

(54) APPARATUS FOR CONDUCTING HIGH-TEMPERATURE LIQUID CHROMOTOGRAPHY ANALYSIS

(75) Inventors: Yuri Gerner, Mendota Heights, MN (US); Carl W. Sims, St. Paul, MN (US); Kurt P. Hamberg, Fridley, MN (US)

(73) Assignee: Systec, Inc., New Brighton, MN (US)

( * ) Notice: Subject to any disclaimer, the term of this patent is extended or adjusted under 35 U.S.C. 154(b) by 0 days.

(21) Appl. No.: 09/967,066

(22) Filed: Sep. 28, 2001

(65) Prior Publication Data

US 2003/0061867 A1 Apr. 3, 2003

(51) Int. Cl.[7] .............................................. G01N 30/02
(52) U.S. Cl. ................................................... 73/61.52
(58) Field of Search .................... 73/61.52; 210/198.2, 210/635, 656; 356/337; 436/180

(56) References Cited

U.S. PATENT DOCUMENTS

| | | |
|---|---|---|
| 4,088,458 A | 5/1978 | Jourdan |
| 4,098,592 A | 7/1978 | Prescott et al. |
| 4,404,845 A | 9/1983 | Schrenker |
| 4,478,720 A | 10/1984 | Perrut |
| 4,599,169 A | 7/1986 | Ray |
| 4,917,575 A | 4/1990 | Miller, Jr. et al. |
| 5,028,243 A | 7/1991 | Rubey |
| 5,038,852 A | 8/1991 | Johnson et al. |
| 5,094,741 A | 3/1992 | Frank et al. |
| 5,169,521 A | 12/1992 | Oka et al. |
| 5,215,556 A | 6/1993 | Hiller et al. |
| 5,238,557 A | 8/1993 | Schneider et al. |
| 5,322,626 A | 6/1994 | Frank et al. |
| 5,944,877 A | 8/1999 | O'Neil |
| 6,175,409 B1 * | 1/2001 | Nielsen et al. .............. 356/337 |

* cited by examiner

Primary Examiner—Helen Kwok
Assistant Examiner—Jay L Politzer
(74) Attorney, Agent, or Firm—Haugen Law Firm PLLP

(57) ABSTRACT

A system for conducting high-temperature liquid chromatographic analysis includes a mobile phase transport tube configured to operably convey mobile phase from a source to respective chromatographic instruments in the system, a pre-heater apparatus operably coupled to the mobile phase transport tube for heating the mobile phase to a desired temperature, a chromatographic column operably coupled to the pre-heater apparatus, and including temperature-maintaining means for maintaining the column at a pre-determined temperature and a counter-flow heat exchanger operably exchanging heat from outlet mobile phase to inlet mobile phase through conductive heat transfer means. In a particular embodiment, the mobile phase passing through the chromatographic column is maintained in a substantially adiabatic environment.

13 Claims, 9 Drawing Sheets

APPARATUS FOR CONDUCTING HIGH-TEMPERATURE LIQUID CHROMOTOGRAPHY ANALYSIS

FIELD OF THE INVENTION

The present invention relates to liquid chromatography systems generally, and more particularly to systems for conducting chromatographic analysis at high temperatures. This invention also relates to methods for performing chromatographic analysis on liquid samples at elevated or high temperatures.

BACKGROUND OF THE INVENTION

A number of liquid chromatography systems are in use today, which systems utilize a variety of configurations specifically tailored to particular chromatographic applications. In many of such applications, elevated temperatures have been determined to be helpful in the elution of liquid samples in mobile phases. As a general matter, increased temperature of the liquid mobile phase correspondingly lowers mobile phase viscosity, which allows an increased mobile phase flow rate through the liquid chromatography system while maintaining desired chromatographic analysis attributes. As a result, a number of liquid chromatography systems in use today utilize heating means for elevating the mobile phase temperature as the mobile phase is directed through the system.

Liquid chromatography heating instrumentation and design has typically been confined to the temperature range of ambient to 60° C., and flow rates from zero to three milliliters per minute, as dictated by the particular materials making up the chromatographic systems. A specific limitation to existing chromatographic systems for processing mobile phase streams at elevated temperatures is the packing material utilized in the liquid chromatography columns. Such packing material is typically a silica or less typically a polymer-based material. Silica-based materials are chemically and thermally unstable at temperatures above 100° C., while polymeric materials tend to swell or change shape causing problems in use. Therefore, more temperature-resistant materials must be utilized in order to allow chromatographic analysis of liquid mobile phases above 60° C.

An example of such a thermally-stable material is zirconia which provides relatively stable analytical separations at temperatures even in excess of 200° C. In fact, recent tests have demonstrated that packing materials utilizing zirconia as the substrate material are chemically and thermally stable at temperatures approaching the critical point of water (375° C.).

The significantly raised temperature limits of the mobile phase in liquid chromatography systems made possible by such packing materials provide a number of advantages over typical, relatively low-temperature (<60° C.) chromatography systems. For example, high-temperature mobile phase liquids reflect a correspondingly lower viscosity, such that flow rate through the chromatographic column may be increased while maintaining a substantially laminar flow regime. In addition, advantageous solvent properties may be realized at such elevated or high temperatures. Water, for example, increasingly resembles an organic solvent as temperature increases toward the critical temperature of water. In fact, recent tests and calculations indicate that at 250° C., water exhibits solvent properties approaching those of the pure organic solvents most commonly used in liquid chromatography applications, such as methanol and acetonitrile. Thus, in reversed phase applications, the transfer of the solute from pure water to the stationary phase at high temperature (200° C.) resembles that of the transfer of a solute from a pure organic eluent to the stationary phase at 25° C. The use of only water as a mobile phase is environmentally and economically highly desirable. Further, the decrease in viscosity of water at temperatures above 100° C. may be exploited by substantially increasing mobile phase flow rates, as compared to standard temperature chromatographic systems, thereby substantially decreasing analysis time. Such flow rate increases are made possible by the lower viscosity which correspondingly decreases the back pressure of the mobile phase within the chromatographic column. The decreased back pressure allows increased throughput flow rate without exceeding the mechanical pressure limits of the liquid chromatograph pumping system. A further advantage of high-temperature chromatography is providing the analyst additional means to optimize sample separation and increase resolution of various analytes.

Chromatographic heating systems in use today, however, are generally operated below 60° C., and as such have a number of disadvantages which compromise the overall efficacy of such high-temperature liquid chromatography. Some existing systems utilize conductive or convective heating to the chromatographic column to impart heat energy to the mobile phase for elevated temperature analysis of samples dissolved therein. Such techniques fail to properly "pre-heat" the mobile phase prior to admission into the chromatographic column, whereby mobile phase temperature profiles are created radially and axially within the chromatographic column. Mobile phase temperature profiles are, in general, undesired in liquid chromatography applications, as such temperature profiles typically result in peak broadening.

Some chromatographic heating systems utilize a radiant or convective oven in which some of the chromatographic instruments are placed for elevating the temperature of the mobile phase being transported to the column. Such ovens are typically relatively large in volume to encompass at least a portion of the chromatographic system in a heated environment, and have varied success in elevating respective temperatures uniformly. For example, the desired temperature may not be reached in all locations within the oven, such that the temperature within respective chromatographic instruments may vary depending upon their positions within the oven. In addition, the temperature within the chromatographic column can vary both radially and axially, due to differences in temperature of the incoming mobile phase as compared to that of the oven. A common problem experienced with oven heating systems is the column temperature varying from the desired temperature set point, due either to temperature gradients within the oven or slow thermal equilibration of the column under actual operating conditions.

One method utilized to minimize such temperature gradient conditions is the use of pre-heater devices for elevating the temperature of the mobile phase before directing the mobile phase into the chromatographic column. Such pre-heaters may be in a variety of forms, though most typically a means for imparting a pre-determined amount of heat energy through conductive or convective means is utilized. Because such pre-heaters are typically programmed to provide a pre-defined amount of heat energy to the mobile phase, adjustment for varying environmental conditions and incoming mobile phase temperatures for elevating the mobile phase to a desired temperature set point is not well accomplished by existing systems. Furthermore, such preheaters are typically not optimized to deliver the heated mobile phase to the chromatographic column at a temperature consistent with gradient-free adiabatic conditions within the column.

It is therefore a principle object of the present invention to provide a system for performing liquid chromatographic analysis at elevated temperatures, wherein temperature gradients in the chromatographic column are minimized.

It is another object of the present invention to provide a chromatographic system for analyzing samples in mobile phases heated above 100° C.

It is a further object of the present invention to provide a high-temperature chromatographic system which utilizes heated mobile phases in a substantially adiabatic environment through a chromatographic column.

It is a yet further object of the present invention to provide a high-temperature liquid chromatography system in which external energy required to sufficiently heat the mobile phase is minimized.

It is a still further object of the present invention to provide a high-temperature liquid chromatography system having counter-flow heat exchange means for utilizing heat energy stored in mobile phase exiting the chromatographic column.

It is another object of the present invention to provide a load-responsive system which is capable of dynamically adjusting energy input at various locations in the system to achieve desired set point temperatures in various mobile phase flow regimes.

Another object of the present invention is to provide a high-temperature liquid chromatography apparatus having one or more temperature-control means for maintaining respective chromatographic instruments at desired temperature set points.

It is a still further object of the present invention to provide a liquid chromatography system having temperature stabilizing means operably coupled to a chromatographic column for maintaining a substantially adiabatic environment between the column and the heated mobile phase passing therethrough.

It is a further object of the present invention to provide a liquid chromatographic system having one or more temperature-sensing means for regulating various temperatures in the system, including the elevated-temperature mobile phase.

It is a still further object of the present invention to provide a high-temperature liquid chromatography system utilizing, in combination, a counter-current heat exchanger placing inlet and outlet mobile phase in thermal contact with one another, a pre-heater apparatus for elevating the inlet mobile phase to a desired set point temperature, and a temperature stabilizing device operably coupled to a respective chromatographic column for maintaining a substantially adiabatic environment between the column and the mobile phase passing therethrough, such that temperature gradients within the column are minimized.

SUMMARY OF THE INVENTION

By means of the present invention, an improved high-temperature liquid chromatography apparatus is provided for analyzing samples utilizing or dissolved within liquid mobile phases subcritical at temperatures in excess of 100° C. The system of the present invention is preferably configured to minimize temperature gradients within the chromatographic column, such that a substantially adiabatic environment is obtained between the column and the elevated-temperature mobile phase passing therethrough. By performing such liquid chromatography at temperatures exceeding 100° C., it has been found that it is possible to decrease the proportion of organic solvents in aqueous mobile phases, or, depending on the sample, utilize water as a sole solvent in the mobile phase, which correspondingly provides economic and environmental benefits over the existing use of organic solvents in liquid chromatography applications.

One embodiment of the system for conducting high-temperature liquid chromatographic analysis includes a mobile-phase transport tube configured to operably convey mobile phase from a mobile phase source to respective chromatographic instruments in the system, a pre-heater apparatus operably coupled to the mobile phase transport tube for heating the mobile phase to a desired temperature, and a chromatographic column operably coupled to, and disposed downstream from, the pre-heater apparatus, wherein the chromatographic column includes temperature stabilizing means associated therewith for maintaining the column in a substantially adiabatic environment with the mobile phase passing therethrough. The pre-heater apparatus may include a conductive heating element disposed adjacent to the mobile phase transport tube, and one or more temperature sensing means adapted to determine the temperature of respective components of the pre-heater apparatus, as well as the mobile phase therein. The temperature sensing means are preferably operably coupled to temperature control means, or power input control means, which are adapted to regulate the power input to the heating element so as to maintain the respective elements at predetermined set point temperatures. The chromatographic column preferably includes a column heating apparatus for maintaining the column at a desired set point temperature, wherein the column set point temperature is substantially equal to the mobile phase temperature entering the column.

Another embodiment of the high-temperature chromatography system includes a mobile phase inlet conduit configured to operably convey mobile phase from a mobile phase source to the system, a pre-heater apparatus operably coupled to the mobile phase inlet conduit for heating the mobile phase to a desired temperature, a chromatographic column operably coupled to the pre-heater apparatus, wherein the chromatographic column includes insulation means for maintaining the column at a temperature consistent with the mobile phase passing therethrough, and a mobile phase outlet conduit configured to operably convey the mobile phase from the column, a portion of the outlet conduit being disposed in propinquant relationship with a portion of the inlet conduit in a heat exchange zone, such that a counter-flow heat exchanger is created between respective portions of the inlet and outlet conduits in the heat exchange zone, whereby heat contained in the outlet mobile phase is conductively transferred to the inlet mobile phase.

The present invention also contemplates a method for analyzing liquid samples in a high-temperature chromatographic environment. The method includes providing a mobile phase inlet conduit configured to operably convey mobile phase from a mobile phase source to respective chromatographic instruments, providing a pre-heater apparatus operably coupled to the mobile phase inlet conduit for heating the mobile phase to a desired temperature, providing a chromatographic column operably coupled to the pre-heater apparatus, whereby the column includes insulation means for maintaining the column at temperatures consistent with the mobile phase passing therethrough, and providing a mobile phase outlet conduit configured to operably convey the mobile phase from the column, wherein a portion of the outlet conduit is disposed in a thermally conductive relationship with a portion of the inlet conduit in a heat exchange zone, such that counter-flow heat exchanger is created between respective portions of the inlet and outlet conduits in the heat exchange zone. The method includes utilizing a mobile phase pump to inject mobile phase into the mobile phase inlet conduit and through respective chromatographic instruments, and allowing heat to dissipate into the inlet mobile phase from the outlet mobile phase in the heat exchange zone through conductive heat transfer. The mobile phase is then further heated in the pre-heater apparatus to a first pre-determined set point, and thereafter the sample dissolved within the mobile phase is chromatographically separated in the column at an elevated temperature of at least 100° C., which elevated temperature is maintained in a substantially adiabatic state throughout an entire length of the column. The mobile phase is then cooled in the heat exchange zone through conductive heat transfer to the inlet mobile phase. The cooled and chromatographically separated sample is then analyzed in an appropriate chromatographic detector downstream from the heat exchange zone.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
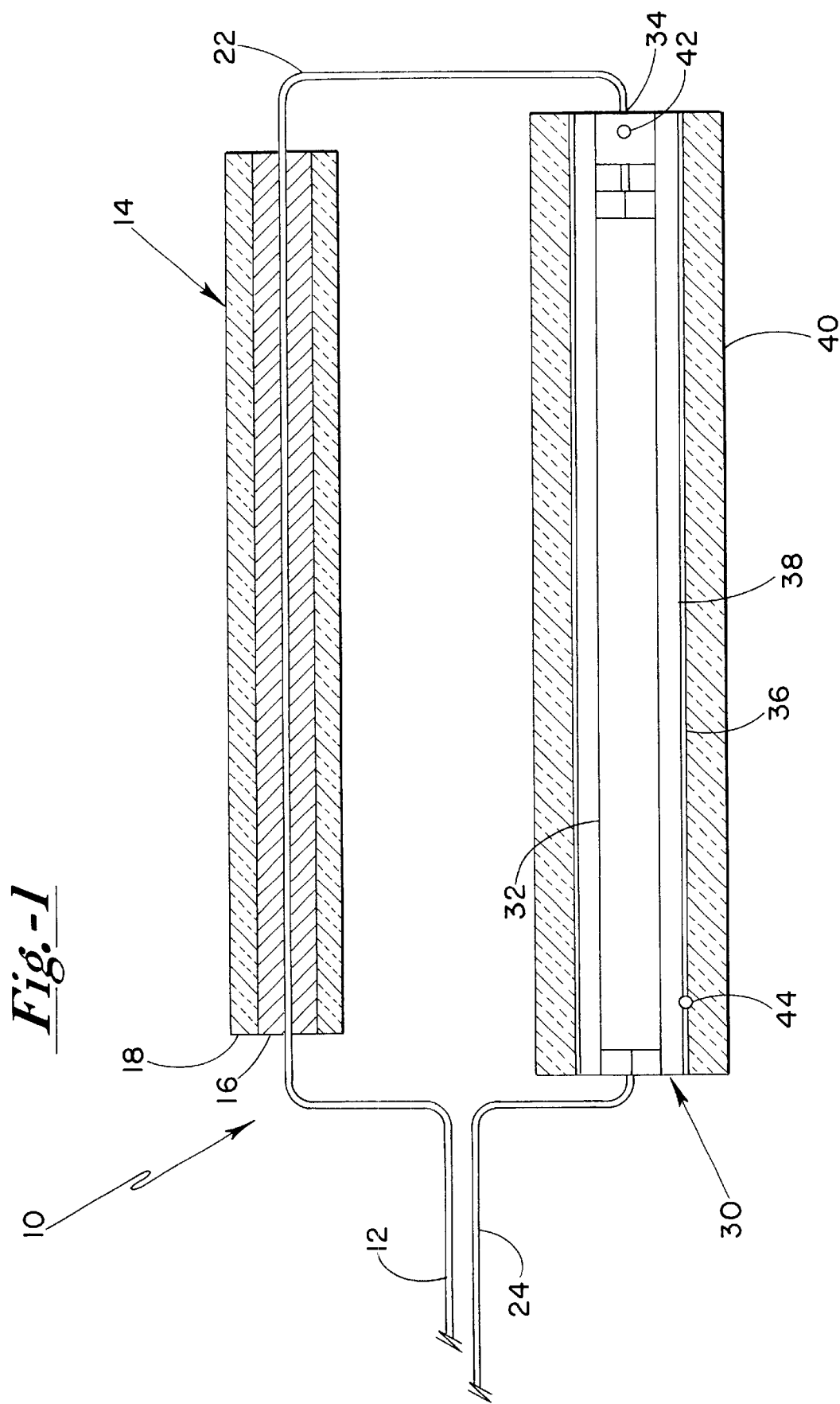
FIG. 1 is a schematic diagram showing core components of one embodiment of the present invention.

Referring now by characters of reference to the drawings, and first to FIG. 1, a chromatographic heating system 10 is shown. System 10 preferably includes a mobile phase inlet conduit 12 for conveying mobile phase from a source (not shown) to respective liquid chromatography instruments. Conduits for transporting the mobile phase through system 10 are preferably durable and are relatively immune to degradation effects caused by various mobile phases passing therethrough. Such conduit materials include, for example, stainless steel, titanium, Hastelloy C-22, or any other material resistant to degradation or other reactive conditions.

As shown in FIG. 1, mobile phase inlet conduit 12 is directed through a pre-heater apparatus 14, which pre-heater apparatus 14 is configured to impart heat energy to the mobile phase passing therethrough. In preferred embodiments, pre-heater apparatus 14 includes a conductive heating means 16 disposed adjacent to, and in thermal contact with inlet conduit 12. Pre-heater apparatus 14 is thus preferably a conductive heater disposed at least partially circumferentially about inlet conduit 12 for conductively heating the mobile phase flowing through conduit 12. Heat transfer is therefore preferably obtained from heating means 16 to the thermally-conductive conduit 12, and additionally to the mobile phase within conduit 12.

Heating means 16 of pre-heater apparatus 14 is preferably a length of thermally conductive material, which is operably coupled to power input means, such as electrical wires or the like. The materials making up heating means 16 are preferably configured to convert electrical input into heat energy, which is easily dissipated to conduit 12. In preferred embodiments, heating means 16 is both physically and thermally coupled to interiorly-disposed mobile phase conduit 12 via a thermally-conductive adhesive or solder. In preferred embodiments, however, the solder utilized to braze heating means 16 to conduit 12 comprises a mixture of silver, copper, and zinc, but may comprise any materials suitable as a bonding solder which desirably has a melting point above 250° C.

Heating means 16 may reflect a variety of configurations, though the configuration illustrated in FIG. 1 is most preferred, with heating means 16 at least partially surrounding mobile phase conduit 12 for conductive heating thereto. Heating means 16 is preferably any relatively thin device which is capable of converting electrical input to thermal energy with a relatively high degree of efficiency. In preferred embodiments, heating means 16 is about 90% efficient in transferring 50 watts of energy to the mobile phase. In some embodiments, heating means 16 is configured to impart up to 150 watts of energy to the mobile phase, though embodiments having greater energy transfer rates are contemplated as well. The length of heating means 16 disposed along mobile phase conduit 12 is preferably sufficient to impart a desired amount of thermal energy to the mobile phase being heated thereby. In a particular embodiment, pre-heater apparatus 14 is configured to provide sufficient energy to heat 5 ml/min of mobile phase from ambient to between 200 and 250° C.

Pre-heater apparatus 14 preferably includes insulation material 18 surrounding heating means 16. As shown in FIG. 1, insulation material 18 preferably circumferentially surrounds heating means 16 to thereby inhibit thermal energy losses to the environment. Insulation material 18 may be comprised of a variety of thermally insulative materials, and is most preferably a fiberglass or other mineral-based material. Other insulative materials may be utilized in insulation layer 18 which are suitable for thermal insulation properties at high-temperature conditions, such as foamed polymers including silicone and poly-imide.

A transfer portion 22 of mobile phase conduit 12 preferably conveys the mobile phase from pre-heater apparatus 14 to a chromatographic column apparatus 30. Transfer portion 22 of conduit 12 is preferably short in length to minimize thermal losses through conduit wall 12 to the environment. Transfer portion 22 of the conduit 12 preferably conveys the mobile phase to an inlet 34 of column 32.

Chromatographic column apparatus 30, as shown in FIG. 1, includes a column which is preferably adapted for use in liquid chromatography applications, whereby appropriate packing materials useful in causing chromatographic separations of liquid samples are contained within column 32. Column apparatus 30 of the present invention preferably includes a column thermal shield heater 36 disposed at least partially around column 32. In preferred embodiments, an internal insulation layer 38 proximately surrounds column 32, and is disposed between column 32 and thermal shield heater 36. In other embodiments, however, thermal shield heater 36 may be disposed directly adjacent to column 32 without internal insulation layer 38 disposed therebetween. Internal insulation layer 38 may comprise any thermally insulative material, though a fiberglass or other mineral-based insulation, or other suitable high-temperature foamed polymer such as silicone or poly-imide is particularly desirable for insulating chromatographic instruments of the present invention.

In preferred embodiments of the present invention, column apparatus 30 is configured such that column 32 maintains a constant temperature throughout its length, which temperature is consistent with the temperature of the mobile phase at inlet 34. In such a manner, column apparatus 30 maintains a substantially adiabatic environment between column 32 and the mobile phase passing therethrough. To maintain such a constant temperature throughout the column length, thermal shield heater 36 is disposed at least partially circumferentially around column 32 for maintaining column 32 itself at a temperature substantially equal to the mobile phase therewithin, as well as to replace thermal energy lost from the mobile phase and from column 32 to the environment. As such, thermal shield heater 36 preferably comprises a thermally conductive material in the form of a heating jacket at least partially encompassing column 32, which thermally-conductive material is operably coupled to power input means, such as electrical wires. In a particular example, thermal shield heater 36 comprises a copper jacket operably coupled to electrical wires, which connect heater 36 to a power source (not shown). In operation, the power input acts to elevate the temperature of thermal shield heater 36, such that conductive heat transfer to column 32 may be accomplished.

In preferred embodiments, an external insulation layer 40 at least partially surrounds thermal shield heater 36 for thermally insulating heat generated thereby. Heat losses to the environment from thermal shield heater 36, column 32, and the mobile phase are preferably minimized by effectively isolating the high-temperature elements of the present invention from the ambient environment. Therefore, external insulation layer 40 preferably provides a high degree of insulative properties to column apparatus 30.

Column apparatus 30 is preferably configured such that a substantially adiabatic environment is created between column 32 and the mobile phase passing therethrough, though embodiments adding heat from thermal shield heater 36 to the mobile phase are also contemplated by the present invention. In such a manner, the temperature of the incoming mobile phase at inlet 32 is desirably maintained throughout the entire length of column 32. Therefore, heat content within thermal shield heater 36 is only maintained, and not added to. To facilitate the maintenance of a substantially adiabatic environment, a mobile phase temperature probe 42 is provided adjacent to column inlet 34 for determining the temperature of the incoming mobile phase. Mobile phase temperature probe 42 is preferably operably coupled to a power input controller, which controls the power input to thermal shield heater 36. As such, mobile phase temperature probe 42 assists in adjusting the power input to thermal shield heater 36 to thereby maintain column 32 at a temperature substantially equal to the mobile phase throughout an entire length of column 32. Mobile phase temperature probe 42 is preferably a typical thermocouple-type device, which is adapted to measure temperature and deliver a corresponding electrical signal to the operably coupled power input controller. Most preferably, mobile phase temperature probe 42 is disposed adjacent to inlet 34 of column 32, such that temperature gradients within column 32 are minimized throughout an entire length thereof.

In some embodiments of the present invention, mobile phase temperature probe 42 may comprise transfer portion conduit 22 itself, in that the material comprising the tubing may act as at least a portion of a thermal couple-type device. In such a manner, the length of conduit 22 may be correspondingly minimized so as to reduce heat loss to the environment prior to entering column apparatus 30.

Means are preferably provided for allowing system 10 to be "load responsive", in that the amount of heat energy supplied to respective heating elements in system 10 is calibrated for mobile phase flow rate and composition. Through such load response means, system 10 automatically and dynamically adjusts heat input to accomplish desired temperature set points for inputted mobile phase flow rate and composition characteristics.

In preferred embodiments, column apparatus 30 of the present invention further includes a thermal shield temperature probe 44 operably coupled to thermal shield heater 36 and the power input control means (not shown). Thermal shield temperature probe 44 is preferably adapted to determine the temperature of thermal shield heater 36 to thereby provide the power input control means with information relevant to maintaining a substantially adiabatic environment between column 32 and the mobile phase passing therethrough. Preferably, thermal shield temperature probe 44 is adapted to deliver electrical impulse information generated by a thermocouple-type device making up temperature probe 44, which electrical impulses are interpreted by the power input control means to correspondingly adjust the power input to thermal shield heater 36. Preferably, thermal shield temperature probe 44 is disposed distally from mobile phase temperature probe 42, such that temperature gradients within column apparatus 30 may be correspondingly minimized.

As shown in FIG. 1, mobile phase outlet conduit 24 preferably conveys the mobile phase exiting column apparatus 30 to further respective chromatographic instruments, including a chromatographic detector (not shown). Mobile phase outlet conduit 24 is preferably fabricated from the same material as used in inlet conduit 12 and transfer portion 22, such that consistent, if any, effects on the mobile phase due to interaction with respective conduits may be maintained.

Figure 2:
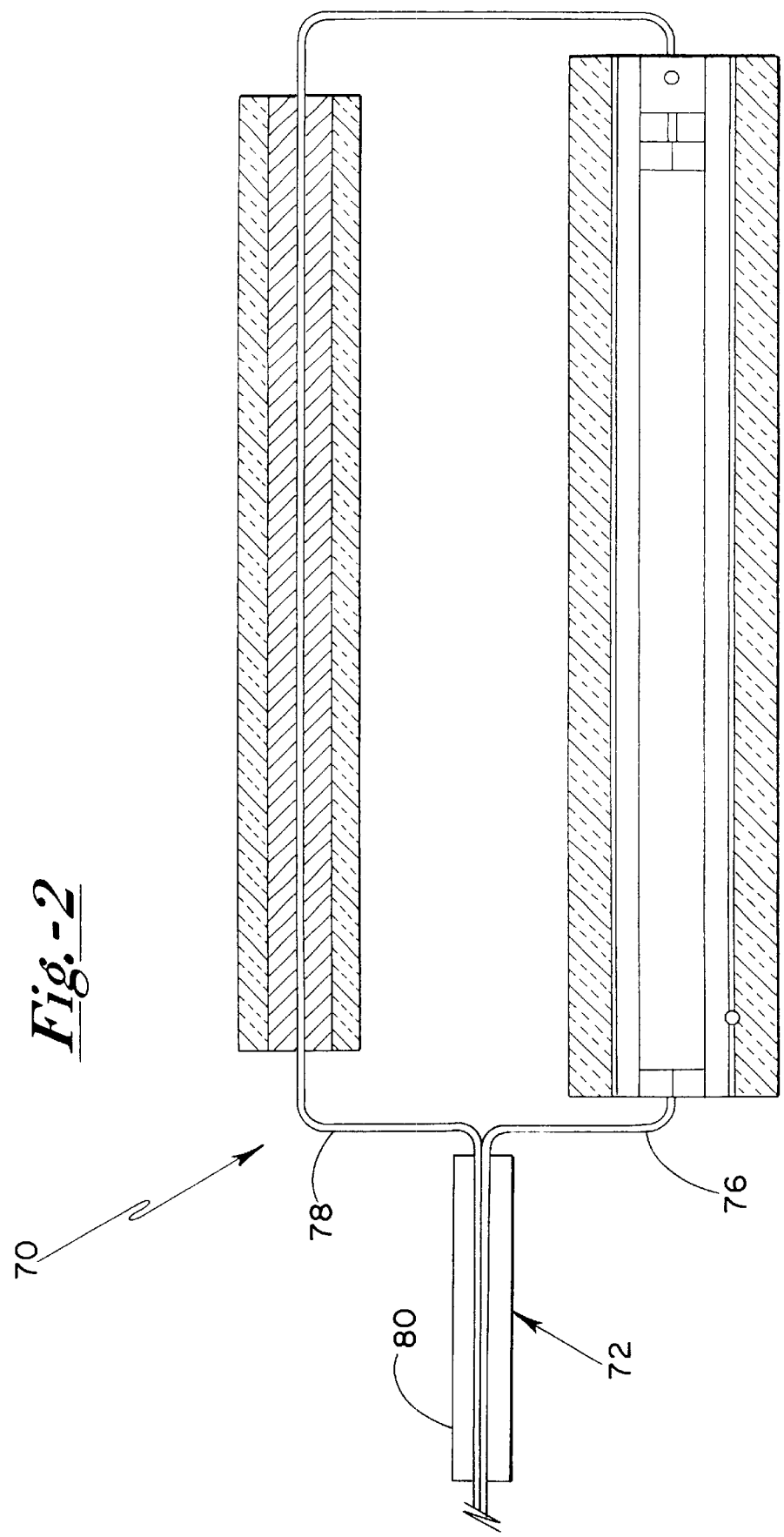
FIG. 2 is a schematic diagram showing core components of an alternate embodiment of the present invention.

With attention now being drawn to FIG. 2, a system 70 which is similar to the system 10 illustrated in FIG. 1 is shown. Chromatographic system 70, however, includes a counter-flow heat exchanger 72 which is configured to transfer heat from the outlet mobile phase in outlet conduit 76 to the inlet mobile phase passing through inlet conduit 78.

Preferably, outlet conduit 76 and inlet conduit 78 are disposed in thermal contact in heat exchanger 72. Most preferably, such mobile phase conduits are bonded together in heat exchanger 72 by a thermally-conductive adhesive or solder, such as a solder mixture of silver and copper having a melting point above 250° C., though other bonding means are also contemplated by the present invention. In such a manner, heat content stored in the outlet mobile phase and outlet conduit 76 may be effectively transferred to inlet mobile phase and inlet conduit 78 in heat exchanger 72. Through such a heat exchange method, incoming mobile phase is heated before entering respective chromatographic instruments while the outgoing mobile phase is correspondingly cooled prior to analysis in the chromatographic detector (not shown). Since mobile phase contents and flow rates in inlet conduit 78 and outlet conduit 76 are substantially similar, heat transfer characteristics are symmetrical, such that temperature gained by the inlet mobile phase is equally offset by the temperature lost in the outlet mobile phase stream.

In preferred embodiments of the present invention, heat exchanger 72 includes an insulation layer 80 at least partially surrounding the coupled mobile phase conduits. Insulation layer 80 is preferably configured to minimize heat losses to the environment, and instead focus the heat transfer from the outlet mobile phase and outlet conduit 76 to the inlet mobile phase in inlet conduit 78.

Heat exchanger 72 acts to minimize the input heat energy required of the pre-heater apparatus, as well as the thermal shield heater, by initially elevating mobile phase temperature through heat transfer principles from the outlet mobile phase stream. In addition, the outlet mobile phase stream is correspondingly cooled from the elevated temperature of within the chromatographic column, such that the mobile phase is introduced to the chromatographic detector at an appropriate temperature.

Figure 3:
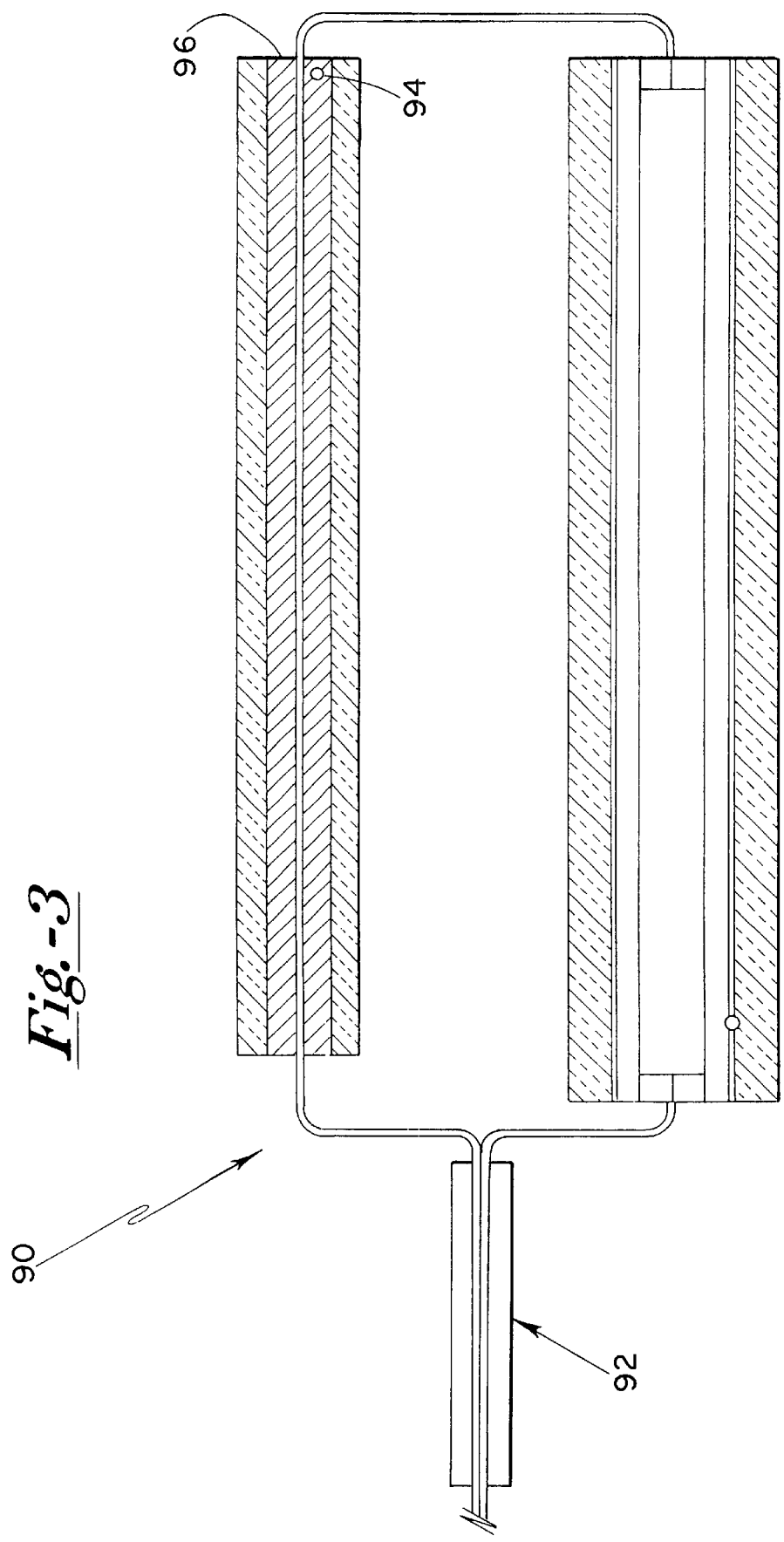
FIG. 3 is a schematic diagram showing the core components of a second alternate embodiment of the present invention.

The embodiment illustrated in FIG. 3 depicts a system 90 similar to those shown in FIGS. 1 and 2, which system 90 includes a heat exchanger 92 for exchanging heat between outlet mobile phase and inlet mobile phase streams. System 90 further includes a pre-heater temperature probe 94 which is operably coupled to heating means 96 and power input control (not shown). Temperature probe 94 preferably monitors the temperature of heater device 96 by means of a thermocouple-type device which provides electrical impulse information to the power input control means based upon the temperature sensed. In such a manner, temperature probe 94, in combination with power input control means, has the capability to maintain heating means 96 at a desired set point temperature, and correspondingly maintain the mobile phase passing therethrough at a desired temperature.

In some embodiments of the present invention, a mobile phase temperature probe may be utilized in combination with, or individually, in the pre-heater apparatus of the present invention. Such a mobile phase temperature probe preferably functions to direct electrical temperature information to a power input control means whereby energy directed to the mobile phase heating means may be correspondingly adjusted to maintain the temperature of the mobile phase exiting the pre-heater apparatus at a desired set point. In particular embodiments, the temperature of the mobile phase exiting the pre-heater apparatus is slightly higher than the steady-state mobile phase temperature desired during analysis in the chromatographic column. Such temperature control of the mobile phase at multiple distinct points throughout the system of the present invention may be accomplished through the utilization of one or more of the above-described temperature probes. Such temperature probes, operating in combination, provide the information necessary for a power input control means to operably adjust power directed to respective system heaters to maintain temperatures at desired set points. Therefore, the temperature probe devices described above, as well as a variety of other temperature probes may be utilized and distributed throughout the system of the present invention to desirably maintain elevated temperatures of both the mobile phase and respective chromatographic instruments throughout the system.

Figure 4:
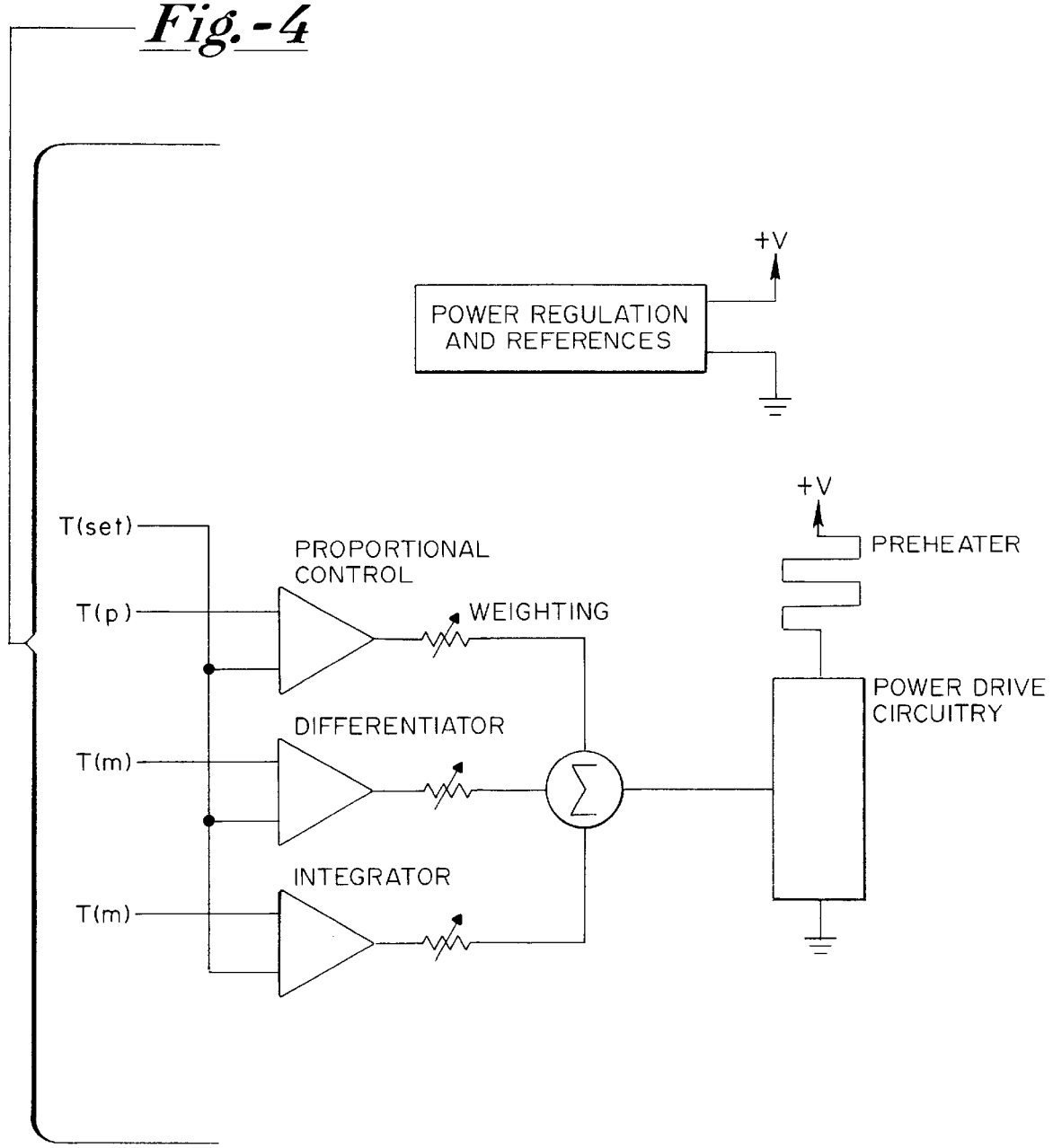
FIG. 4 is a block diagram illustrating an electrical control mechanism for the pre-heater heating element of the present invention.
Figure 5:
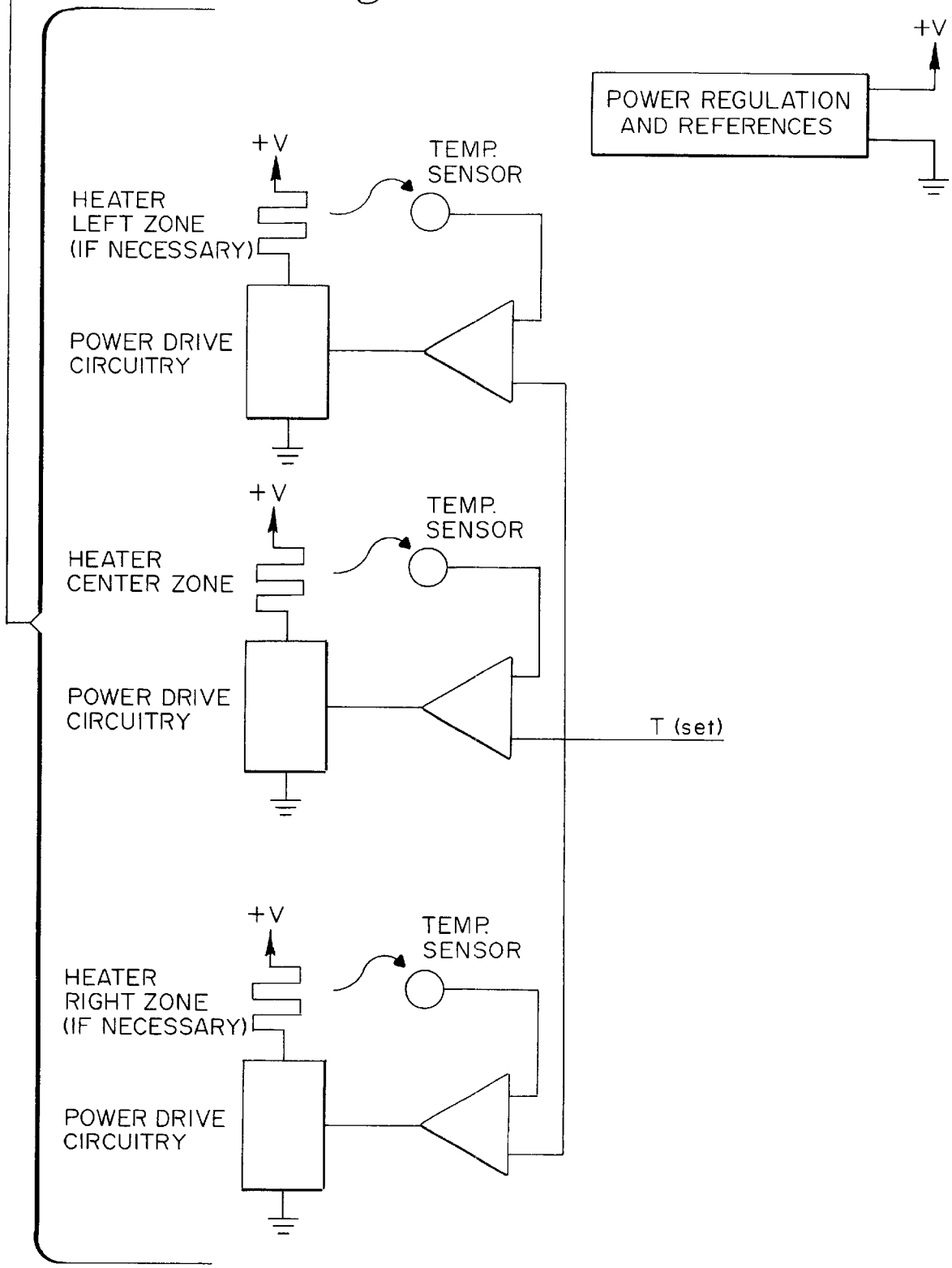
FIG. 5 is a block diagram illustrating an electrical control mechanism for controlling the thermal shield heater in the column apparatus of the present invention.

FIGS. 4 and 5 represent exemplary block diagrams illustrating electrical control means for electrically controlling power input to the pre-heater apparatus and the column thermal shield heater, respectively. FIG. 4 illustrates an electrical control design for the pre-heater apparatus, including an optional integrator mechanism, which may be included in particular applications of the invention. FIG. 5 illustrates electrical temperature control means coupled to the thermal shield heater of the chromatographic column apparatus. As shown in FIG. 5, the thermal shield heater of the present invention may be divided into a plurality of heating zones, which may or may not be individually controlled by distinct electrical control sequences. In other embodiments, electrical control of the thermal shield heater may be driven by fewer or more distinct control sequences than that shown in FIG. 5. In particular applications of the present invention, the power applied to respective heating elements may be proportional to the mobile phase flow rate passing therethrough. In such circumstances, one or more of the heating elements may be heated by pulsed energy inputs. To accurately apply such pulsed power, the mobile phase residence time between respective temperature sensing devices may be timed such that the power input necessary may be calculated as inversely proportional to the mobile phase residence time therein.

Figure 6:
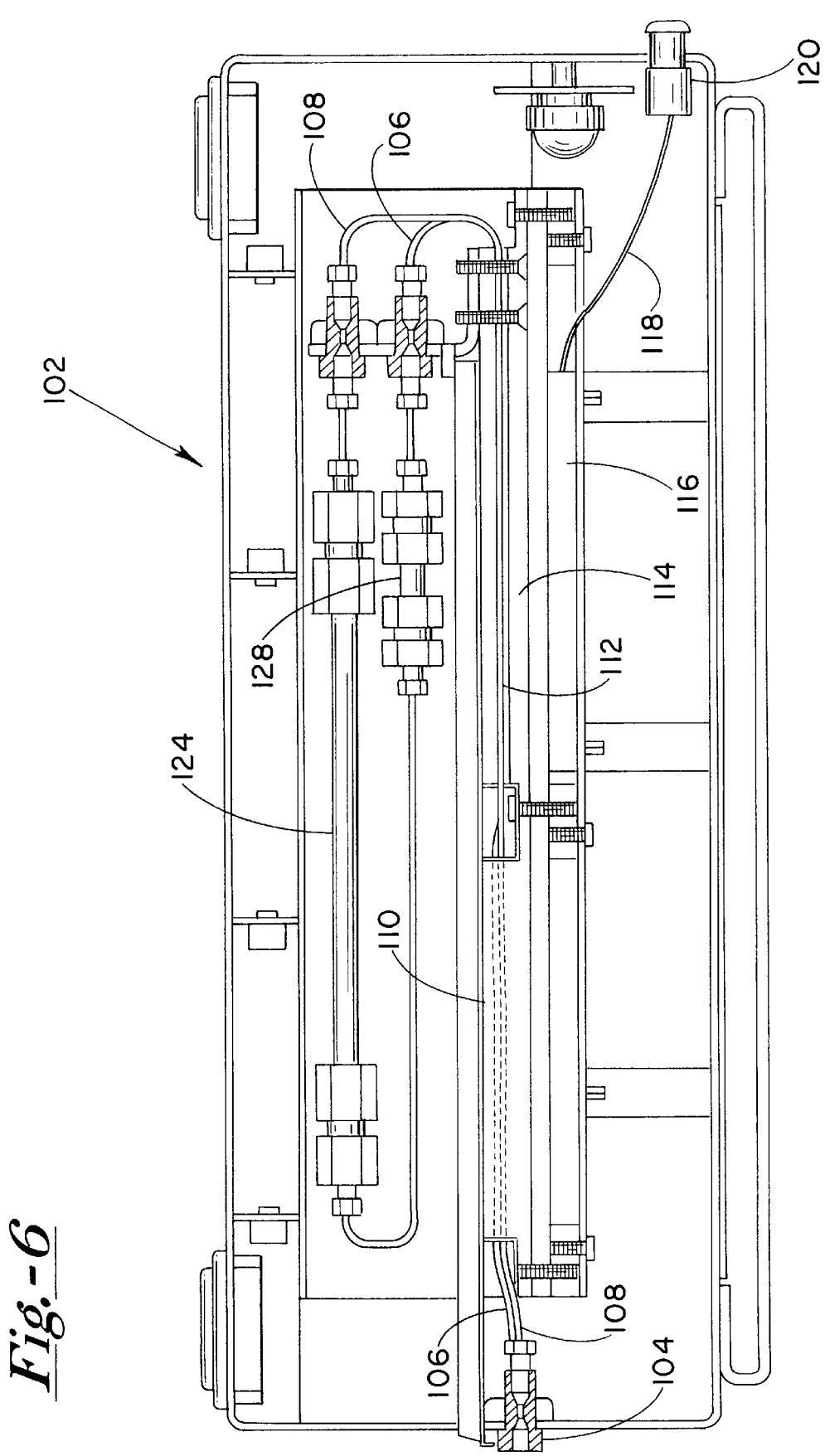
FIG. 6 is a partial cross-sectional view of one embodiment of the present invention.

FIG. 6 illustrates a cross-sectional view of one embodiment of the system of the present invention. Heating system 102, as illustrated in FIG. 6, shows mobile phase inlet and outlet ports 104, which inlet and outlet ports 104 communicate with additional components of a liquid chromatography system. Inlet conduit 106 and outlet conduit 108 are placed in isolated thermal contact with one another in heat exchanger 110. In such a manner, inlet mobile phase flowing through conduit 106 is heated prior to introduction into pre-heater apparatus 112. Pre-heater apparatus 112 provides thermal energy transferred to the inlet mobile phase through preferably conductive heat transfer means. Thermal energy is provided to the mobile phase via a thermally conductive strip 114 such as aluminum or copper, which strip 114 is conductively heated by a cartridge heater 116 disposed adjacent thereto. Cartridge heater 116 is preferably operably coupled to an electrical connector device 120 via electrical wire 118 or the like. Pre-heated mobile phase is then transported via conduit 106 through various coupling means to chromatographic column 124. In a particular embodiment of the present invention, a guard column 128 is provided for regulating mobile phase flow into column 124.

Figure 7:
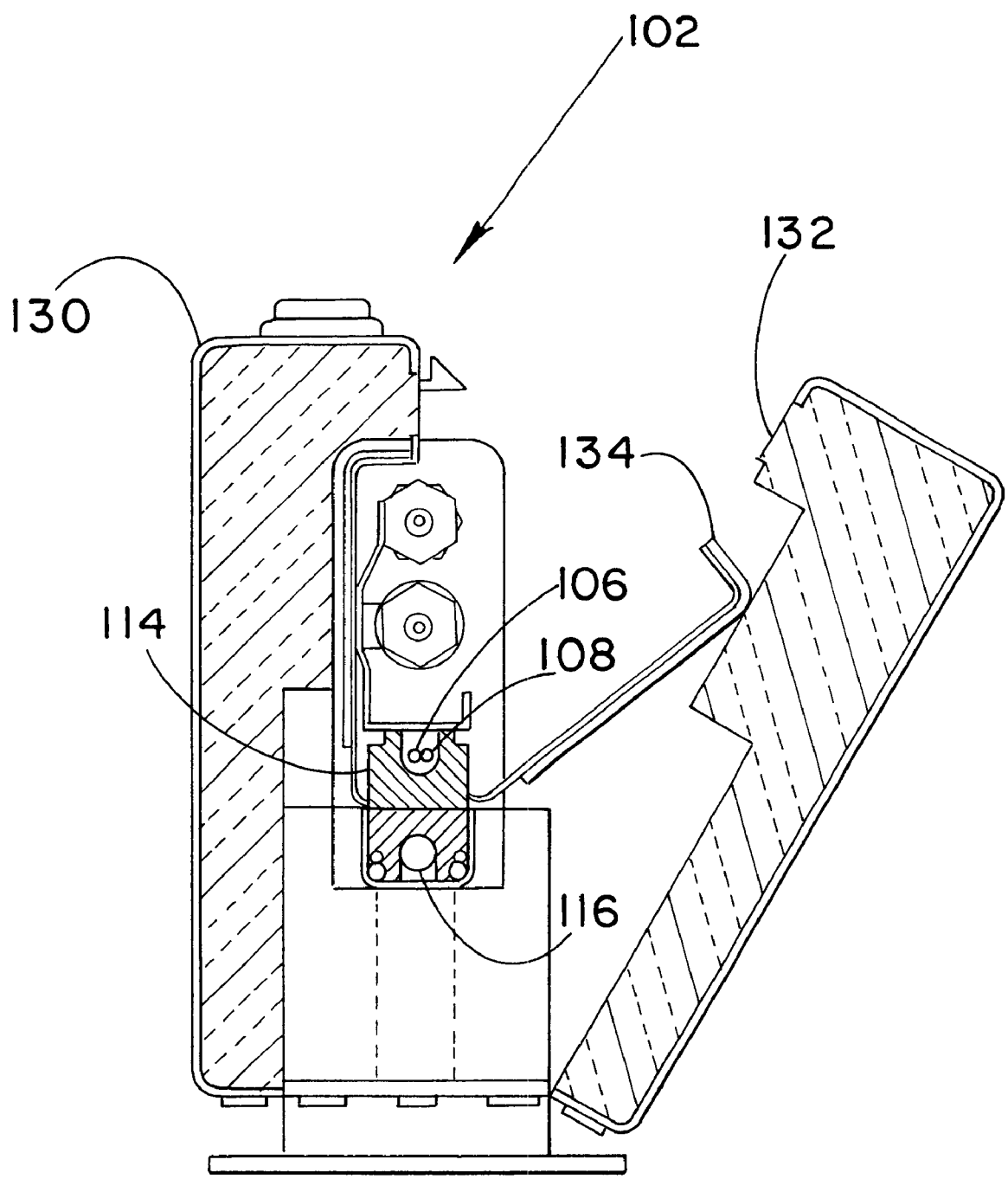
FIG. 7 is a partially cut-away end view of the embodiment illustrated in FIG. 6.

FIG. 7 illustrates a cut-away end view of system 102, as illustrated in FIG. 6. As can be seen more clearly in FIG. 7, cartridge heater 116 preferably includes a heated core surrounded by a thermally conductive material, such as copper or aluminum. Heater strip 114 is positioned immediately adjacent to cartridge heater 116, such that conductive heat transfer is efficiently accomplished. Conduits 106 and 108 are shown in FIG. 7 as being in thermal contact adjacent to heater strip 114. A variety of other heat transfer configurations are contemplated by the present invention.

As illustrated in FIG. 7, system 102 may comprise a selectively sealable enclosure 130 having an outer, insulated cover 132, and an inner, sealable chamber 134 in which the heated components of the present invention preferably reside. When closure 134 is sealed, a temperature-controlled environment may be obtained therewithin. In such a manner, consistent elevated-temperature chromatographic analysis may be achieved in the insulated enclosure 130. As illustrated in FIG. 7, enclosures 132 and 134 are each selectively sealable, such that excess heat may be quickly disseminated after analysis is completed. Further, access to specific chromatographic components for service or cleaning may be easily obtained through the selective closure means of the present invention.

Figure 8:
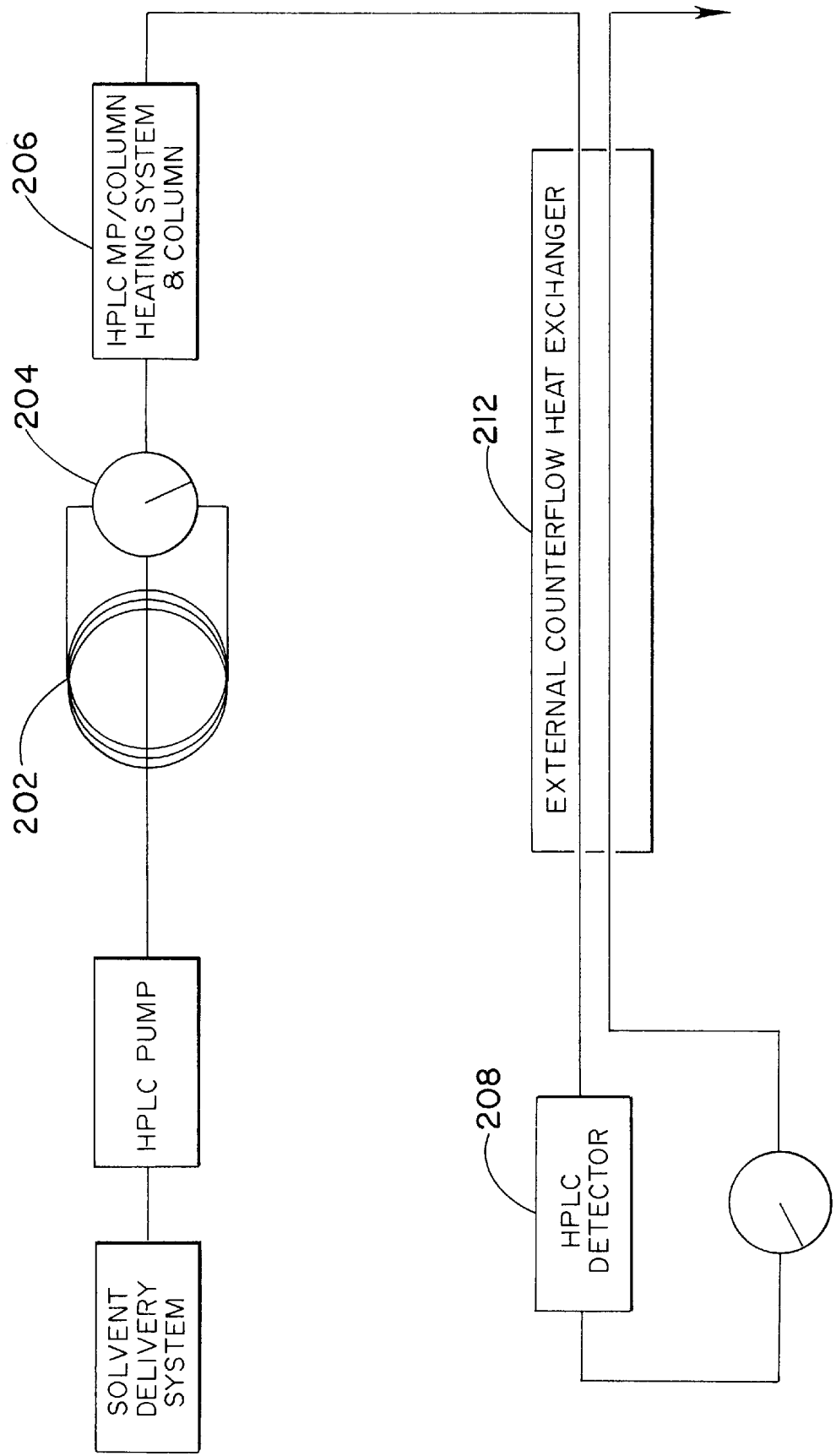
FIG. 8 is a schematic diagram illustrating an overall chromatographic system in accordance with the present invention.
Figure 9:
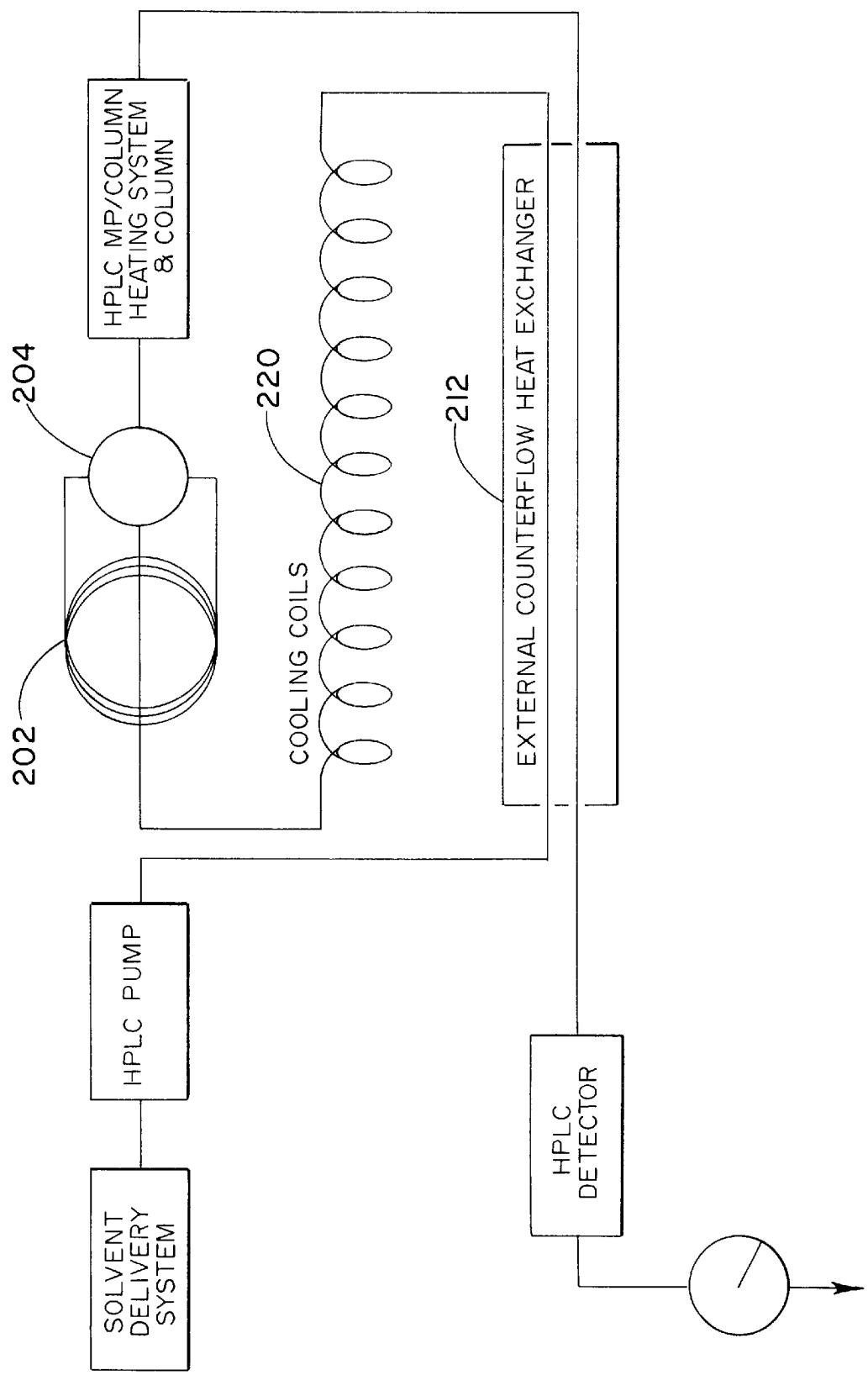
FIG. 9 is a schematic diagram illustrating an alternative embodiment of a chromatographic system in accordance with the present invention.

Exemplary overall chromatographic systems incorporating the heating systems of the present invention are illustrated in FIGS. 8 and 9. With reference to FIG. 8, a solvent delivery system including a liquid chromatography pump are utilized to inject sample to the system of the present invention via an injection valve loop 202 and injection valve 204. Through such a solvent delivery system, a metered flow rate of mobile phase is preferably provided to the heating system of the present invention. In the embodiment illustrated in FIG. 8, outlet mobile phase exiting heating system 206 of the present invention is directed through an external counter-flow heat exchanger 212 prior to delivery to an HPLC detector 208 for desirably cooling the mobile phase before reaching the detector. External heat exchanger 212 may incorporate an independent fluid stream for efficiently cooling the mobile phase. Such cooling is desired to protect sensitive equipment in the chromatographic detector, which may be damaged by mobile phase having a temperature exceeding 100° C. To drive the external counter flow heat exchanger 212, a pump or back pressure regulator is provided to sustain sufficient mobile phase flow through the counter-current portion of the heat exchanger 212.

A further embodiment contemplated by the present invention includes directing inlet mobile phase through an external counter-flow heat exchanger 212 prior to delivery to injection valve loop 202 and injection valve 204. In such a manner, enhanced heat exchange cooling may be obtained between the inlet and outlet mobile phase streams, such that the outlet mobile phase being directed to the chromatographic detector is further cooled by exchanging heat with inlet mobile phase initially entering counter flow heat exchanger 212 at ambient temperature. In some embodiments, cooling coils 220 may be provided to adequately protect injection valve 204 from excessive mobile phase temperatures passing therethrough. Such cooling coils 220 may include cooled water tubes, or other cooling fluids.

In operation, the system of the present invention preferably receives mobile phase from an injection valve at a rate of between 1 milliliter per minute and about 20 milliliters per minute, and more preferably between about 3 milliliters per minute and about 10 milliliters per minute. Such mobile phase flow is driven by a liquid phase pump of typical construction. In some embodiments of the invention, flow rates exceeding 20 milliliters per minute are envisioned, so long as adequate heating means are provided to elevate the mobile phase temperature to a preferably subcritical temperature of at least about 100° C. prior to admission to the chromatographic column. The inlet mobile phase is preferably routed through a counter-flow heat exchanger, wherein heat contained in outlet mobile phase is preferably transferred to the inlet mobile phase stream to thereby raise the temperature of the inlet mobile phase. The inlet mobile phase is then preferably directed through a pre-heater apparatus, wherein a conductive heating element is disposed at least partially circumferentially around the inlet mobile phase conduit. Heat generated by the pre-heater apparatus is preferably conductively transferred to the inlet mobile phase through the mobile phase conduit.

The heated mobile phase is preferably directed into a chromatographic column apparatus having temperature stabilization means including a thermal shield heater which is capable of conductively transferring heat to the chromatographic column. In preferred embodiments, however, the chromatographic column is maintained at a temperature substantially equal to the temperature of the mobile phase at the column inlet, such that temperature gradients experienced by the mobile phase throughout its passage through the chromatographic column are minimized. In such a manner, the chromatographic column maintains a substantially adiabatic environment between the column wall and the mobile phase passing therethrough. The elevated temperature mobile phase exiting the chromatographic column is then preferably directed through a counter-flow heat exchanger to disseminate heat contained within the outlet mobile phase to incoming mobile phase.

In preferred embodiments of the present invention, one or more temperature sensing means are positioned at various locations in the system to monitor respective temperatures, and to indicate such temperature to power input control means, such that the power input control means may adjustably control power input to respective heat-generating devices in the system.

A number of distinct advantages over existing systems are introduced by the system of the present invention. A primary advantage brought about by the present invention is the capability of the present liquid chromatography system to heat and analyze samples in mobile phases at temperatures exceeding 100° C., which temperatures are preferably subcritical. At such elevated temperatures, solvents used in mobile phase streams have substantially lower viscosities, such that the mobile phase flow rate through the system may be correspondingly increased without detrimentally affecting heat transfer or chromatographic analysis characteristics. By increasing mobile phase flow rate through the system, analysis time required in the system is also correspondingly reduced. Chromatographic analysis characteristics, however, are not detrimentally affected by the decrease in mobile phase residence time in the system because of the enhanced temperature effects on chromatographic resolution. Indeed, increased mobile phase temperature correspondingly increases the theoretical plate count in respective chromatographic columns, such that separations may be adequately resolved in a shorter column distance. As such, the resolving power of a respective chromatographic column is increased proportionally with increased mobile phase temperature. Therefore, column length and analysis time may be substantially reduced in an elevated-temperature environment without detrimentally affecting chromatographic results.

In addition to being advantageous to overall chromatographic system configurations, elevated temperature chromatography may allow the increased use of water as a solvent in the mobile phase. In fact, at temperatures exceeding 200° C., water may be used as the only solvent in the mobile phase, such that economic and environmental benefits over organic solvents are realized.

A particular advantage of the present invention is the minimization of energy input required to heat and maintain the mobile phase passing through the chromatographic system at a temperature of at least 100° C. In the present system, incoming mobile phase is preferably initially heated in a heat exchange zone, wherein elevated temperature outlet mobile phase is brought into thermal contact with the inlet mobile phase for conductive heat transfer therebetween. Such heat transfer raises the temperature of the inlet mobile phase so that energy input required by downstream instruments is correspondingly reduced. The system of the present invention preferably utilizes a conductive pre-heater apparatus for further elevating the inlet mobile phase to a desired temperature set point at which the mobile phase is preferably maintained through downstream chromatographic columns. Once the temperature of the mobile phase has been elevated to the desired temperature set points, the system of the present invention preferably utilizes temperature-maintenance means at least partially surrounding the chromatographic column, whereby a substantially adiabatic environment is created between the column and the mobile phase passing therethrough. The adiabatic column design minimizes energy input required to the column because a substantial portion of the thermal energy is provided by the mobile phase itself. Therefore, energy is only required to maintain the column at a specified temperature substantially equal to that of the mobile phase. The adiabatic configuration further minimizes temperature gradients within the chromatographic column, whereby the temperature of the mobile phase at the column inlet is substantially equal to the mobile phase temperature exiting the column. Minimization of temperature gradients correspondingly optimizes resolution of chromatographic separation obtained in the column. Therefore, the system of the present invention is configured to minimize the energy load necessary to conduct high-temperature chromatographic analysis.

A further advantage of the present invention is the utilization of one or more temperature sensing devices located at various positions along the chromatographic apparatus, which sensors are operably coupled to dynamically-controlled power input control means for adjustably setting the power input to respective heating means on an automated basis. Therefore, temperature set points and mobile phase composition and flow rate information may be pre-defined by system operators, and subsequently carried out by the automated temperature control means of the present invention. In a particular application, a temperature set point of the mobile phase exiting the pre-heater apparatus may be pre-defined at a value equal to, or greater than the temperature set point defined throughout the chromatographic column, such that heat losses from the mobile phase between the pre-heater apparatus and the column apparatus may thereby be accounted for. In some embodiments, the temperature sensing means, in combination with the power input control means, allows system administrators to define and control system temperatures at various points throughout the system.

An additional advantage of the present invention is the utilization of a low-mass configuration, including reduced chromatographic column lengths and reduced heating zone lengths while maintaining desired chromatographic characteristics. Through such a low-mass system, a decrease in power input is needed to increase mobile phase temperatures to desired levels as compared to relatively higher-mass systems. In an alternative embodiment, energy input to the low-mass system may be optimized to substantially decrease the ramp-up time required to reach the desired temperature set point. Heating elements such as nickel-chrome tubing, which itself conveys the mobile phase, may be used to transfer the heating energy to more quickly heat the mobile phase. Such tubing may comprises materials other than the nickel-chrome combination, so long as the mass and resistivity values are consistent with rapid heating of the mobile phase passing therewithin.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A system for conducting high-temperature liquid chromatographic analysis, comprising:
   (a) a mobile-phase transport tube configured to operably convey mobile-phase from a mobile-phase source to chromatographic instruments in said system;
   (b) a pre-heater apparatus operably coupled to said mobile-phase transport tube for heating the mobile-phase to a first pre-determined set point temperature;
   (c) a chromatographic column operably coupled to, and disposed downstream from, said pre-heater apparatus such that the mobile-phase exiting said pre-heater apparatus is directed to said column through said mobile-phase transport tube, said chromatographic column having temperature stabilizing means associated therewith for maintaining said column and said mobile phase therewithin at a second pre-determined set point temperature;
   (d) a first temperature sensing means operably coupled to said pre-heater apparatus for determining the temperature of the mobile phase passing through said pre-heater apparatus;
   (e) a first temperature control means operably coupled to said first temperature sensing means, said first temperature control means being adapted to regulate power input to said pre-heater apparatus, such that the temperature of the mobile phase is maintained at said first pre-determined set point;
   (f) a second temperature sensing means operably coupled to said column and being adapted to operably determine the temperature of the mobile phase passing therethrough; and
   (g) a second temperature control means operably coupled to said second temperature sensing means and said column temperature stabilizing means, said second temperature control means being adapted to regulate power input to said column temperature stabilizing means such that the temperature of the mobile phase passing through said column is maintained at said second pre-determined set point, said first and second temperature control means being operably coupled to one another so as to dynamically maintain said column in a substantially adiabatic relationship with the mobile phase passing therethrough.

2. A system as in claim 1 wherein said pre-heater apparatus includes a conductive heating element disposed adjacent to said mobile phase transport tube.

3. A system as in claim 2 wherein said heating element is at least partially circumferentially disposed about said transport tube.

4. A system as in claim 3 wherein said pre-heater apparatus includes insulative material disposed at least partially circumferentially around said heating element.

5. A system as in claim 1 wherein said first temperature sensing means determines the temperature of the mobile phase exiting said pre-heater apparatus.

6. A system as in claim 1 wherein the mobile phase sustains a substantially constant elevated temperature throughout an entire length of said column.

7. A system as in claim 1, including insulation material disposed at least partially circumferentially around said column.

8. A system as in claim 1 wherein said column temperature stabilizing means is disposed at least partially circumferentially around said column.

9. A system as in claim 8, including internal and external insulation layers, said internal and external layers encompassing said column temperature stabilizing means such that said internal insulation layer is disposed adjacent to and at least partially circumferentially around said column, and said external insulation layer is disposed adjacent to and at least partially circumferentially around said column temperature stabilizing means.

10. A system as in claim 1 wherein said first predetermined set point is substantially equal to said second predetermined set point.

11. A system as in claim 1 wherein said first predetermined set point is higher than said second predetermined set point.

12. A system as in claim 1, including a third temperature sensing means operably coupled to said column heating apparatus for determining the temperature thereof.

13. A system as in claim 8 wherein said second temperature control means is further operably coupled to said third temperature sensing means for dynamically controlling temperatures thereat.

* * * * *

UNITED STATES PATENT AND TRADEMARK OFFICE
CERTIFICATE OF CORRECTION

PATENT NO.     : 6,601,438 B2
DATED          : August 5, 2003
INVENTOR(S)    : Yuri Gerner et al.

It is certified that error appears in the above-identified patent and that said Letters Patent is hereby corrected as shown below:

<u>Title page,</u>
Item [54], Title, "CHROMOTOGRAPHY" should be -- CHROMATOGRAPHY --

Signed and Sealed this

Twenty-fifth Day of November, 2003

JAMES E. ROGAN
*Director of the United States Patent and Trademark Office*